US00PP16667P2

(12) United States Plant Patent
Trees

(10) Patent No.: US PP16,667 P2
(45) Date of Patent: Jun. 20, 2006

(54) ***VERBENA* PLANT NAMED 'BALAZREVE'**

(50) Latin Name: *Verbena hybrida*
Varietal Denomination: Balazreve

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 103 days.

(21) Appl. No.: 11/017,174

(22) Filed: Dec. 20, 2004

(51) Int. Cl.
*A01H 5/00* (2006.01)

(52) U.S. Cl. ..... Plt./308
(58) Field of Classification Search ..... Plt./308
See application file for complete search history.

*Primary Examiner*—Anne Marie Grunberg
(74) *Attorney, Agent, or Firm*—Wood, Phillips, Katz, Clark & Mortimer

(57) ABSTRACT

A new and distinct cultivar of *Verbena* plant named 'Balazreve' characterized by its dark red-colored flowers, dark green-colored foliage, good basal branching character, and mounding and trailing growth habit.

1 Drawing Sheet

Latin name of genus and species of plant claimed: *Verbena hybrida.*
Variety denomination: 'Balazreve'.

BACKGROUND OF THE INVENTION

The present invention comprises a new and distinct *Verbena* plant botanically known as *Verbena hybrida* and hereinafter referred to by the cultivar name 'Balazreve'.

The new cultivar was developed by the inventor through a controlled breeding program during December 2001 at Arroyo Grande, Calif. The objective of the breeding program was the development of *Verbena* cultivars with a semi-trailing mounded habit, continuous flowering, excellent basal branching and small, dark green-colored foliage, and attractive flower coloration.

The female (seed) parent of the new cultivar was the proprietary *Verbena* breeding selection BFP-0970, not patented, which exhibits a semi-trailing growth habit, bright red-colored flowers, and dark green-colored foliage. The male (pollen) parent of the new cultivar was the proprietary *Verbena* breeding selection BFP-1476, not patented, which exhibits a semi-trailing growth habit, red-colored flowers with "eye", and dark green-colored foliage.

One plant within the progeny of the above stated cross-pollination was discovered and selected by the inventor in April 2002.

Asexual reproduction of the new cultivar by terminal stem cuttings in West Chicago, Ill. since April 2002, has demonstrated that the characteristics of the new cultivar, as herein described, reproduce true to type and are firmly fixed and retained through successive generations of such asexual propagation.

SUMMARY OF THE INVENTION

The following characteristics of the new cultivar have been repeatedly observed and can be used to distinguish 'Balazreve' as a new and distinct cultivar of *Verbena* plant:

1. Dark red-colored flowers.
2. Lobed, dark green-colored foliage.
3. Good basal branching character.
4. Mounding and trailing growth habit.

Plants of the new cultivar differ from plants of the female parent primarily in flower color and from plants of the male parent primarily in flower color.

Plants of the new cultivar can be distinguished from plants of its sibling 'Balazwilro', disclosed in concurrent U.S. Plant patent application Ser. No. 11/01,419, in flower color.

Plants of the new cultivar are most similar to the cultivar 'SUNVP-SU', U.S. Plant Pat. No. 10,311. However, in side-by-side comparisons, plants of the new cultivar differ from plants of 'SUNVP-SU' in the following characteristics:

1. The leaves of the new cultivar are a different shape than the leaves of 'SUNVP-SU'.
2. The flowers of the new cultivar are larger than the flowers of 'SUNVP-SU'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ from color values cited in the detailed description, which more accurately describes the colors of 'Balazreve'. The plants were grown in 10 cm pots for 13 weeks in a greenhouse at West Chicago.

DETAILED BOTANICAL DESCRIPTION

Figure 1:
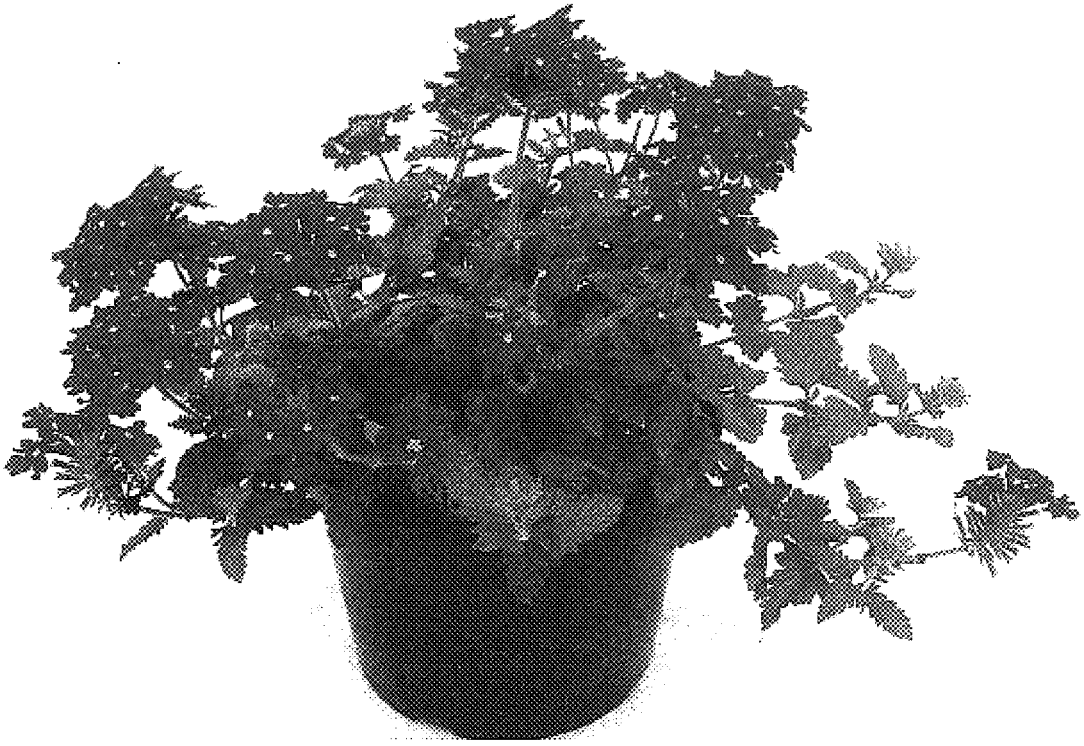
FIG. 1 illustrates a side view of the overall growth and flowering habit of 'Balazreve'.
Figure 2:
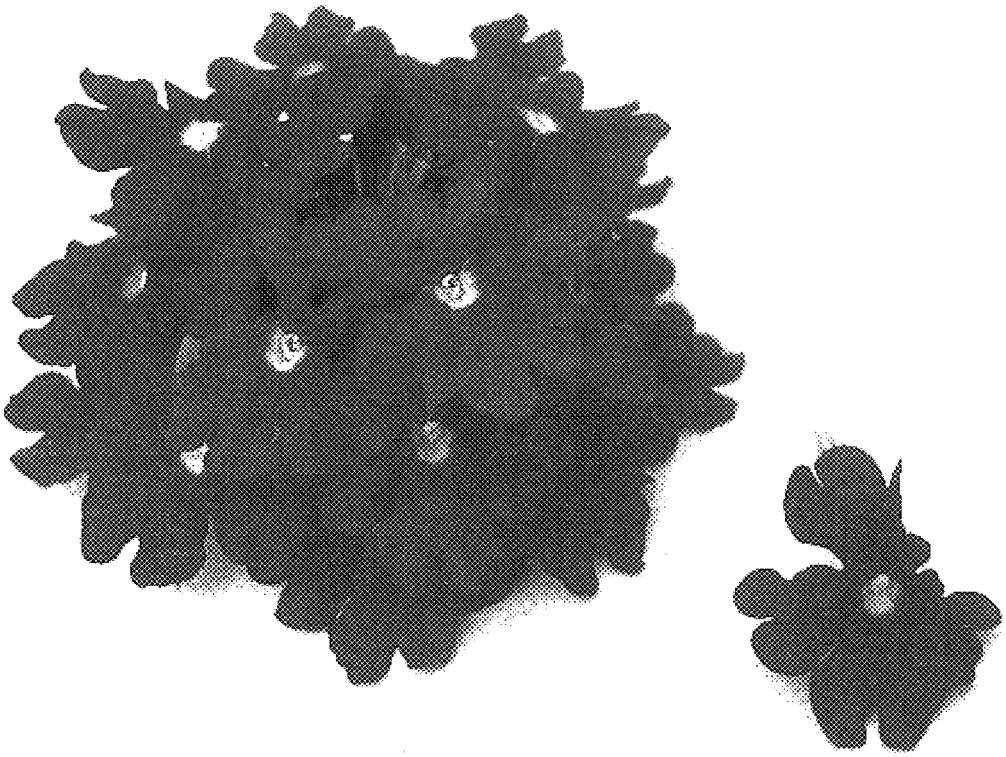
FIG. 2 illustrates a close-up view of an individual inflorescence and single flower of 'Balazreve'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Sep. 24, 2004. The readings were taken between 11:00 and 11:30 a.m. under natural light conditions.

The following descriptions and measurements describe plants produced from cuttings taken from stock plants and grown in a double polycarbonate-covered greenhouse under conditions comparable to those used in commercial practice. Plants were grown at West Chicago, Ill. in 10 cm pots for 13 weeks while utilizing a soil-less growth medium. Greenhouse temperatures were maintained at approximately 70–80° F. (21–26° C.) during the day and approximately 62–65° F. (17–18° C.) during the night. Greenhouse light levels were maintained at approximately 5,000–8,000 foot-candles during the day.

Botanical classification: *Verbena hybrida* cultivar Balazreve.

Parentage:

*Female parent.*—Proprietary breeding selection BFP-0970.

*Male parent.*—Proprietary breeding selection BFP-1476.

Propagation:

*Type cutting.*—Terminal stem.

*Time to initiate roots.*—Approximately 6–9 days.

*Time to produce a rooted cutting.*—Approximately 21–28 days.

*Root description.*—Fibrous.

*Rooting habit.*—Freely branching.

Plant description:

*Crop time.*—Approximately 5–7 weeks from a rooted cutting to finished flowering plant.

*Growth habit.*—Moderately vigorous with good basal branching. Pinching improves basal branching.

*Form.*—Mounding and trailing.

*Size.*—Height from soil level to top of plant plane: Approximately 20.4 cm. Width (area of spread): Approximately 73.2 cm.

*Branch.*—Quantity: Approximately 7 per plant. Shape: Square in cross section. Length from soil level to base of peduncle: Approximately 25.8 cm. Diameter: Approximately 2.4 mm. Texture: Densely pubescent. Color: 145B. Length of internode at middle of branch: Approximately 4.1 cm.

*Foliage.*—Type: Simple. Fragrance: None. Arrangement: Opposite. Orientation to stem: Right angle. Shape: Ovate. Margin: Lobed. Apex: Acute. Base: Truncate. Texture of upper surface: Densely covered with short stiff hairs. Texture of lower surface: Glabrous except for dense pubescence along veins. Leaf length: Approximately 4.1 cm. Leaf width: Approximately 3.2 cm at widest point. Venation pattern: Pinnate. Color of upper surface of mature foliage is darker than 138A with venation of 145B. Color of lower surface of mature foliage: 147B with venation of 145C. Petiole length: Approximately 4.5 mm. Petiole diameter: Approximately 2.3 mm. Petiole texture: Densely pubescent along margin and on lower surface. Color of upper surface: 145B. Color of lower surface: 145C.

Flowering description:

*Flowering habit.*—'Balazreve' is freely flowering under outdoor growing conditions with substantially continuous blooming from spring until autumn and year round in greenhouse environment.

*Inflorescence.*—Type: Corymb. Shape: Hemispherical. Quantity per plant: Approximately 9. Height: Approximately 3.9 cm. Width: Approximately 6.0 cm. Number of fully open flowers per inflorescence at any one time: Approximately 20.

*Peduncle.*—Length: Approximately 6.5 cm. Diameter: Approximately 1.6 mm. Texture: Densely pubescent. Color: Closest to 144A.

*Lastingness of blooms.*—Approximately 5–7 days.

Flower description:

*Bud.*—Rate of opening: Generally, it takes 3–6 days for buds to progress from first color to fully open flower. Shape: Spherical to oval. Length: Approximately 3.9 mm. Diameter: Approximately 3.5 mm. Color: 146A.

*Flower.*—Type: Single, salverform, sessile. Corolla shape: Round. Corolla diameter: Approximately 2.3 cm.

*Petals.*—Quantity: Five, slightly overlapping, fused at base forming tube. Shape: Obovate. Aspect: Slightly cupped. Appearance: Velvety. Margin: Entire. Apex: Emarginate. Texture: Glabrous along margin and in center, pubescent at base. Length: Approximately 1 cm. Width: Approximately 9 mm. Color — Fully opened, upper surface: Between 45A and 46B. Fully open, lower surface: 47B. Whiskers of 155C surround the opening of the corolla tube.

*Corolla tube.*—Length: Approximately 2.0 cm. Diameter at distil end: Approximately 2 mm. Diameter at proximal end: Approximately 0.9 mm. Texture: Pubescent on both surfaces. Color of both inner and outer surfaces: 4D.

*Calyx.*—Shape: Tubular, formed by 5 fused sepals, 5 toothed, 5 ribbed, with stipules. Length: Approximately 1.3 cm. Diameter at apex: Approximately 3.1 mm. Diameter at base: Approximately 1.8 mm. Texture of inner/upper surface: Glabrous. Texture on outer/lower surface: Glandular pubescent. Color of inner/upper — surface: 143D. Color of outer/lower — surface: 143C. Stipule shape: Lanceolate. Stipule apex: Acute. Stipule base: Truncate. Sepal margin: Entire. Stipule length: 6 mm. Stipule texture: Long hairs, some with glands on lower surface, short hairs on upper surface. Stipule color: 146B at base and along mid-vein, 146A at tip and along margin. Gland color: Colorless and transparent.

*Reproductive organs.*—Stamen quantity: 4 per flower. Anther shape: Bilobed, spade like. Anther length: Approximately 0.6 mm. Anther color: 1A. Pollen amount: Moderate. Pollen color: 150D. Pistil quantity: 1per flower. Pistil length: 2 cm. Stigma shape: Funnel. Stigma length: 1.1 mm. Stigma color: 145A. Style length: Approximately 1.7 cm. Style color: 145B. Ovary diameter: 1.8 mm. Ovary color: N144C.

Seed and fruit production: Neither seed nor fruit production has been observed.

Disease and pest resistance: Resistance to pests and pathogens common to *Verbena* has not been observed.

What is claimed is:

1. A new and distinct cultivar of *Verbena* plant named 'Balazreve', substantially as herein shown and described.

* * * * *